(12) United States Patent
Hsieh (10) Patent No.: US 10,736,640 B2
(45) Date of Patent: Aug. 11, 2020

(54) TOURNIQUET WITH PATTERNS OF CAVITIES AND RIDGES ON SURFACES

(71) Applicant: Wheelstone Enterprise Co., Ltd., Taichung (TW)

(72) Inventor: Yung-Lin Hsieh, Taichung (TW)

(73) Assignee: WHEELSTONE ENTERPRISE CO., LTD., Taichung (TW)

( * ) Notice: Subject to any disclaimer, the term of this patent is extended or adjusted under 35 U.S.C. 154(b) by 110 days.

(21) Appl. No.: 16/059,135

(22) Filed: Aug. 9, 2018

(65) Prior Publication Data

US 2020/0046371 A1 Feb. 13, 2020

(51) Int. Cl.
*A61B 17/132* (2006.01)
*A61B 17/00* (2006.01)
*A61B 90/92* (2016.01)

(52) U.S. Cl.
CPC .......... *A61B 17/1322* (2013.01); *A61B 90/92* (2016.02); *A61B 2017/00858* (2013.01); *A61B 2017/00862* (2013.01)

(58) Field of Classification Search
CPC ............ A61B 17/1322; A61B 17/1325; A61B 2017/00858; A61B 2017/00862; A61B 90/92; A61B 17/132; A61F 2013/0028; A61F 2013/00468; A61F 13/08; A61F 13/00; A61F 2013/00238; A61F 2013/00097; D03D 1/00; D03D 13/00; D03D 13/002; D03D 13/004; D03D 13/006; D03D 13/008; D03D 15/08; D03D 17/00; A41D 2400/38; A61H 1/008

USPC ............... 606/201, 202, 203; 602/75, 76, 77
See application file for complete search history.

(56) References Cited

U.S. PATENT DOCUMENTS

| | | | | |
|---|---|---|---|---|
| 1,352,774 | A * | 9/1920 | Angier | A61F 13/00021 604/385.01 |
| 2,082,599 | A * | 6/1937 | Sawyer | A61F 13/0273 602/77 |
| 5,540,714 | A * | 7/1996 | Payne, Jr. | A61B 17/1322 606/201 |
| 5,779,659 | A * | 7/1998 | Allen | A61F 13/00038 602/75 |
| 2007/0267084 | A1 * | 11/2007 | Pereira | D03D 1/00 139/116.1 |
| 2011/0046526 | A1 * | 2/2011 | Evans | A61F 13/00017 602/3 |

(Continued)

*Primary Examiner* — Darwin P Erezo
*Assistant Examiner* — Raihan R Khandker
(74) *Attorney, Agent, or Firm* — Alan D. Kamrath; Karin L. Williams; Mayer & Williams PC (57) ABSTRACT

A tourniquet is presented with a strap including two patterns of cavities and ridges on top and bottom surfaces respectively. The pattern includes a plurality of spaced cavities arranged in parallel rows, the cavity being rectangular and including two first slopes on two short sides respectively and two second slopes on two elongated sides respectively, the first slopes having an elevation greater than that of the second slopes, and the second slopes having an inclined degree greater than that of the first slopes; and a plurality of spaced depressions arranged in parallel rows, the depression being adjacent to the cavity widthwise, the depression being rectangular, and the depression including two third slopes on two short sides respectively and two fourth slopes on two elongated sides respectively. Depths of the cavity and the depression are different.

5 Claims, 8 Drawing Sheets

(56) References Cited

U.S. PATENT DOCUMENTS

| | | | |
|---|---|---|---|
| 2011/0092872 A1* | 4/2011 | Christiansen | A61F 13/0273 |
| | | | 602/53 |
| 2012/0232655 A1* | 9/2012 | Lorrison | A61F 2/0045 |
| | | | 623/13.19 |
| 2013/0172156 A1* | 7/2013 | Inzer | A63B 71/1225 |
| | | | 482/93 |
| 2016/0374686 A1* | 12/2016 | Tihon | A61F 2/0036 |
| | | | 606/157 |
| 2017/0327980 A1* | 11/2017 | Kanoh | D02G 3/12 |

* cited by examiner

TOURNIQUET WITH PATTERNS OF CAVITIES AND RIDGES ON SURFACES

BACKGROUND OF THE INVENTION

1. Field of the Invention

The invention relates to tourniquets and more particularly to a tourniquet having patterns of cavities and ridges on top and bottom surfaces respectively so that the tourniquet can be more slip-resistant.

2. Description of Related Art

Figure 8:
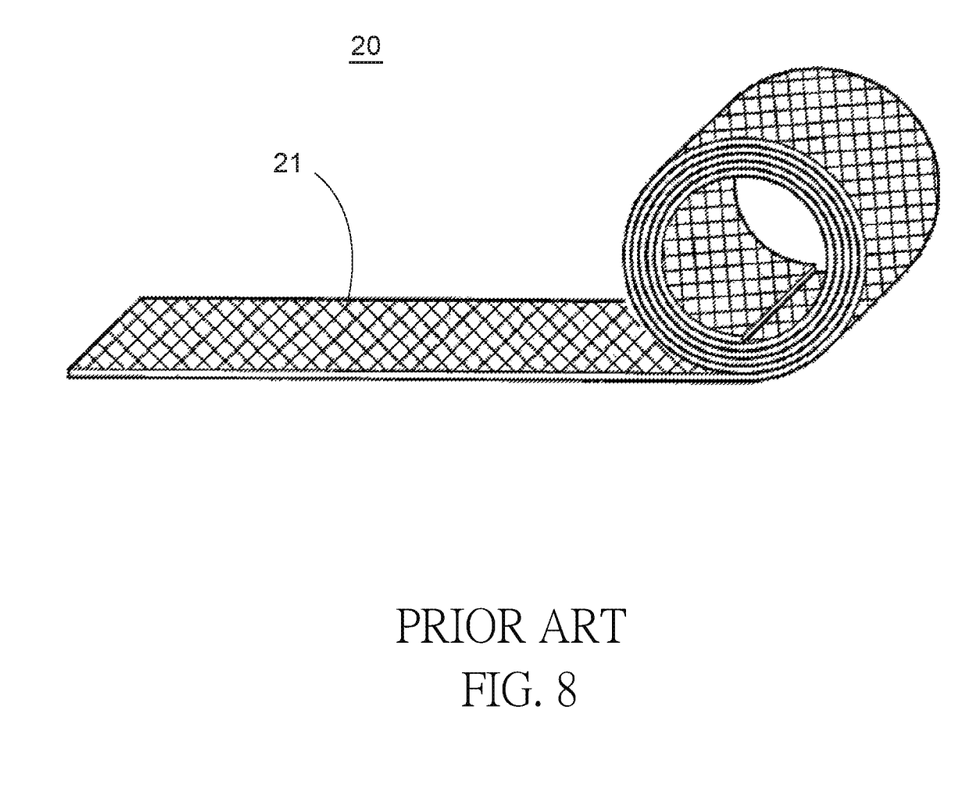
FIG. 8 is a perspective view of a conventional tourniquet.

A conventional tourniquet 20 is shown in FIG. 8 and comprises crisscrosses 21 on top and bottom surfaces respectively. The crisscrosses 21 are formed by adhering two pieces of fabric on top and bottom surfaces of a substrate (e.g., nylon or polyester fiber), sulfurizing them, and separating the pieces of fabric from the substrate respectively. The crisscrosses 21 are slip-resistant in nature.

However, the crisscrosses 21 have crossed lines. Elevation on the short side of the tourniquet 20 is the same as that on the elongated side thereof. It does not help to stretch the tourniquet 20.

Thus, the need for improvement still exists.

SUMMARY OF THE INVENTION

It is therefore one object of the invention to provide a tourniquet for restricting a flow of blood in a body part, the tourniquet comprising a slip-resistant, elongated strap including two patterns of cavities and ridges on top and bottom surfaces respectively, the pattern of cavities and ridges comprising a plurality of spaced cavities arranged in parallel rows, the cavity being rectangular and including two first slopes on two short sides respectively and two second slopes on two elongated sides respectively, the first slopes having an elevation greater than that of the second slopes, the second slopes oriented in a direction the same as that of the strap, and the second slopes having an inclined degree greater than that of the first slopes; and a plurality of spaced depressions arranged in parallel rows, the depression being adjacent to the cavity widthwise, the depression being rectangular, and the depression including two third slopes on two short sides respectively and two fourth slopes on two elongated sides respectively; wherein the cavity has a first depth, and the depression has a second depth less than the first depth; wherein the cavities and the depressions are arranged in alternating fashion; wherein the first slope and the third slope are joined to form a first ridge, and the second slope and the fourth slope are joined to form a second ridge, and the first ridge has an elevation greater than that of the second ridge; and wherein length of the third slope is less than that of the first slope, length of the fourth slope is less than that of the second slope, and length of the fourth slope is greater than that of the first slope.

The invention has the following advantages and benefits in comparison with the conventional art:

Triple slip-resistant effect: The strap is made of slip-resistant material and thus has increased slip-resistance on the surfaces. The cavities are spaced widthwise in each row and thus can increase slip-resistance on the surfaces. Heights of four edges of the rectangular cavities are not the same. The first slope has an elevation greater than that of the second slope. After the strap has been stretched, the first slopes become sharper, thereby further increasing slip-resistance on the surfaces of the strap.

The second slopes are oriented in a direction the same as that of the strap. The second slopes are parallel each other. The second slopes have an inclined degree greater than that of the first slopes. A relatively large force is required to stretch the strap widthwise. Force for stretching the strap lengthwise is not specified. Thus, in response to stretching the strap lengthwise, the first slopes become shorter. And in turn, density of the first slopes is increased. As a result, the first slopes become sharper and the slip-resistance of the surfaces of the strap is increased greatly.

The above and other objects, features and advantages of the invention will become apparent from the following detailed description taken with the accompanying drawings.

DETAILED DESCRIPTION OF THE INVENTION

Referring to FIGS. 1 to 7, a tourniquet in accordance with the invention comprises a slip-resistant, elongated strap 10 including two patterns of cavities and ridges 12 on top and bottom surfaces respectively, the pattern of cavities and ridges 12 being formed of the same material as the strap 10 and formed integrally with the strap 10, the pattern of cavities and ridges 12 including a plurality of spaced cavities 14 arranged in parallel rows, the cavity 14 having a shape similar to a rectangle and having four arcs on its four corners respectively, the cavity 14 having two first slopes 141 on two short sides respectively and two second slopes 142 on two elongated sides respectively, the first slopes 141 having an elevation greater than that of the second slopes 142, the second slopes 142 oriented in a direction the same as that of the strap 10, and the second slopes 142 having an inclined degree greater than that of the first slopes 141.

Figure 1:
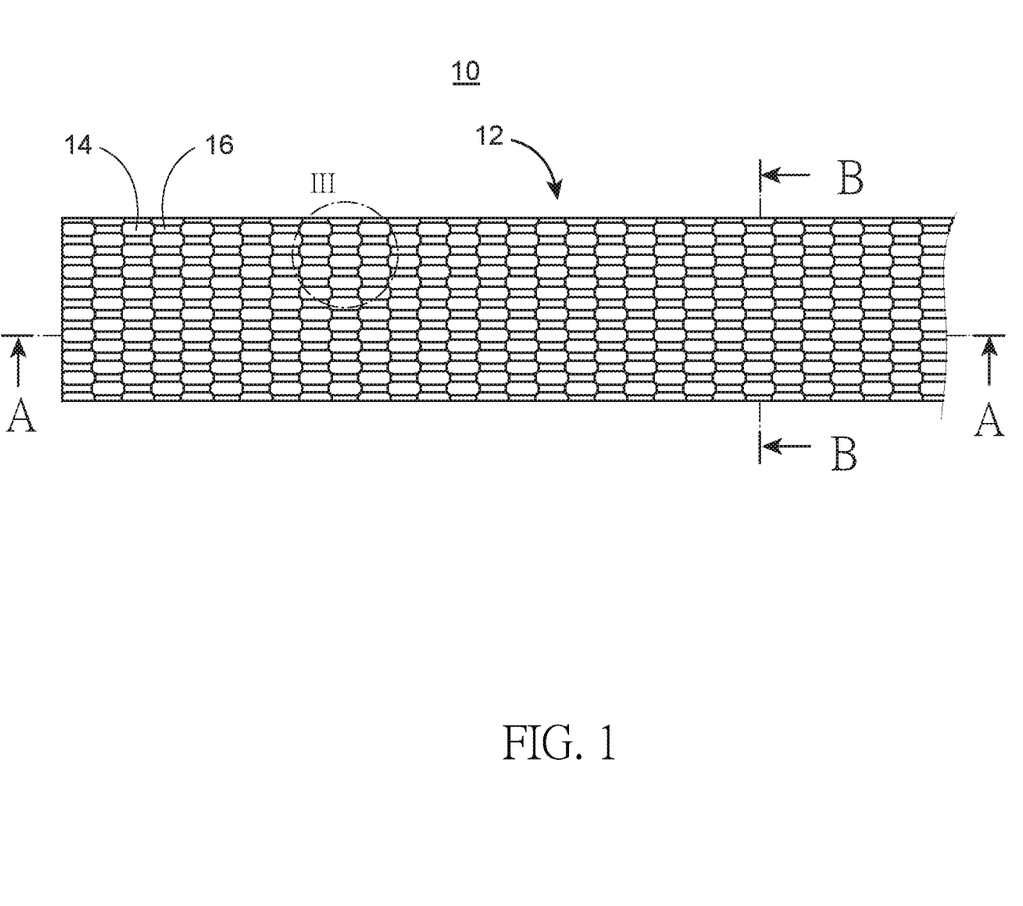
FIG. 1 is a top plan view of a tourniquet according to the invention.
Figure 2A:
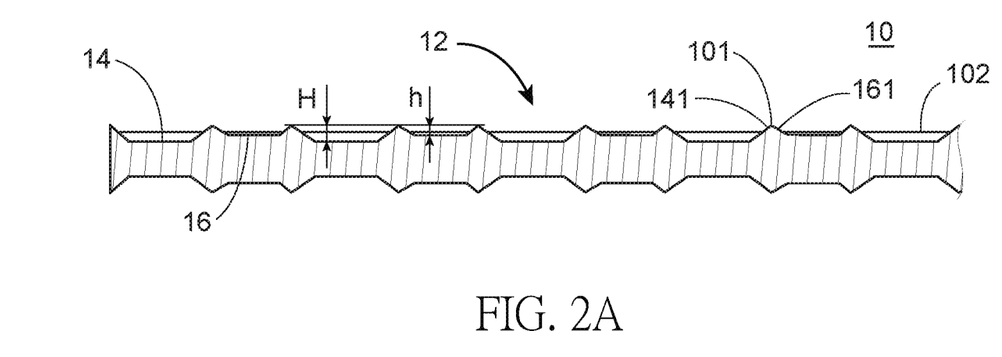
FIG. 2A is a sectional view taken along line A-A of FIG. 1.
Figure 2B:
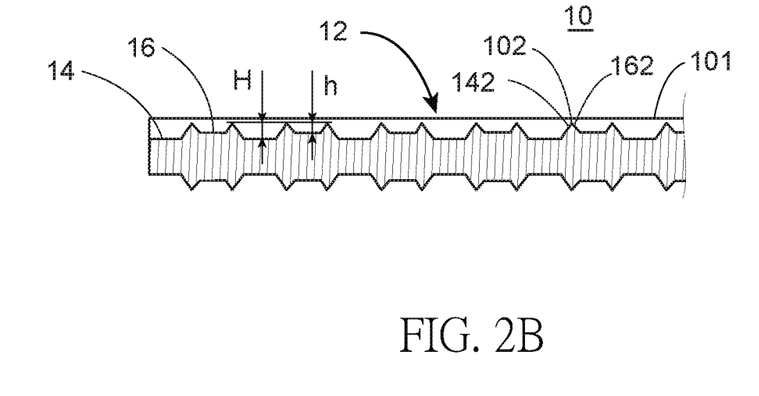
FIG. 2B is a sectional view taken along line B-B of FIG. 1.
Figure 3:
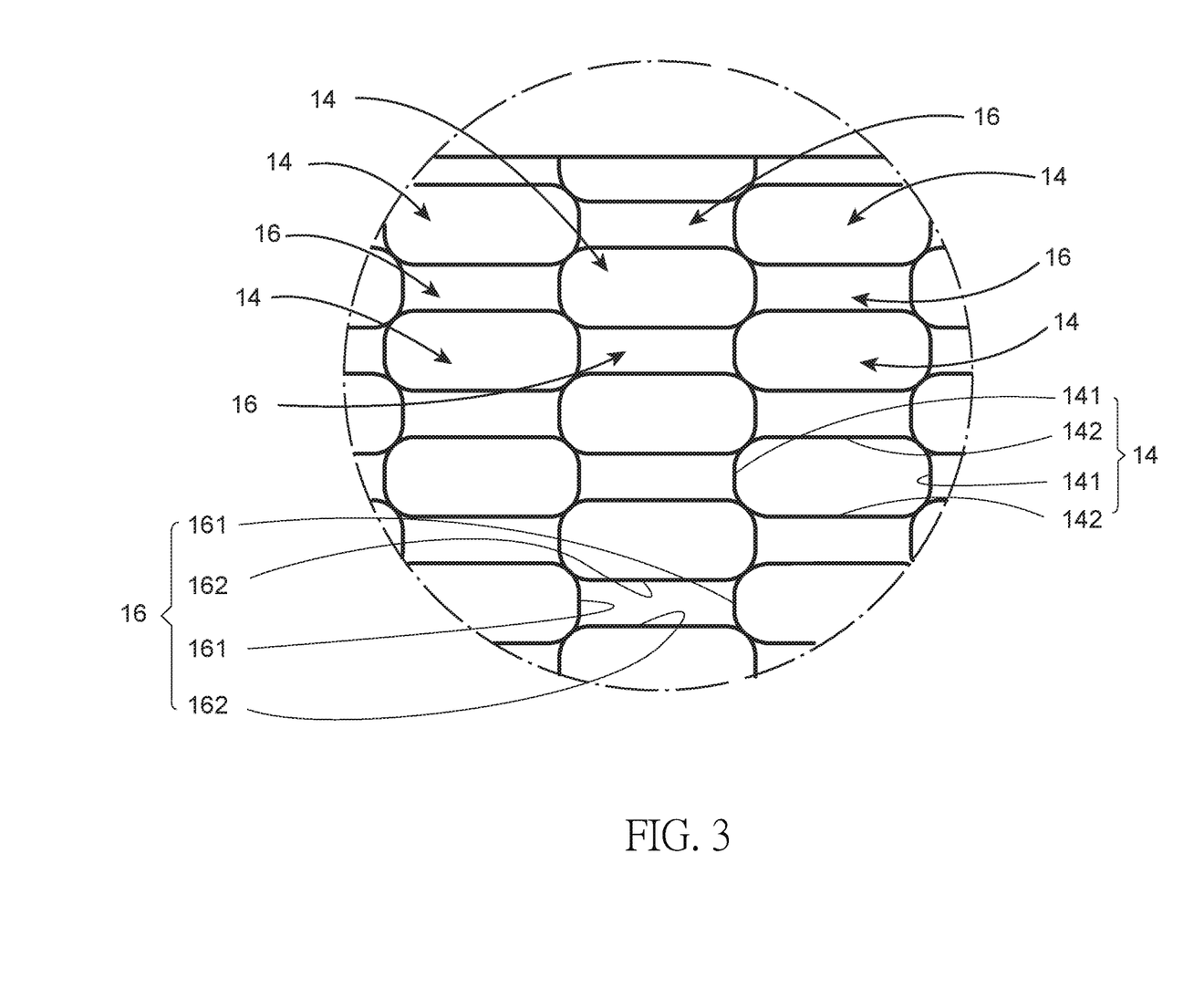
FIG. 3 is a detailed view of the area in circle III of FIG. 1.

As shown in FIGS. 1 to 3 specifically, a plurality of rows of depressions 16 are provided. Each depression 16 is adjacent to the cavity 14 widthwise. The depression 16 has a shape similar to a rectangle and includes two third slopes 161 on two short sides respectively and two fourth slopes 162 on two elongated sides respectively. The cavity 14 has a depth of H and the depression 16 has a depth of h less than H. Length of the third slope 161 is less than that of the first slope 141, length of the fourth slope 162 is less than that of the second slope 142, and length of the fourth slope 162 is greater than that of the first slope 141.

As shown in FIGS. 1 to 3 specifically, the pattern of cavities and ridges 12 includes a plurality of rows of a plurality of the cavities 14 and a plurality of the depressions 16 arranged in alternating fashion. The first slope 141 and the third slope 161 are joined to form a first ridge 101, and the second slope 142 and the fourth slope 162 are joined to form a second ridge 102. The first ridge 101 has an elevation greater than that of the second ridge 102.

Figure 4:
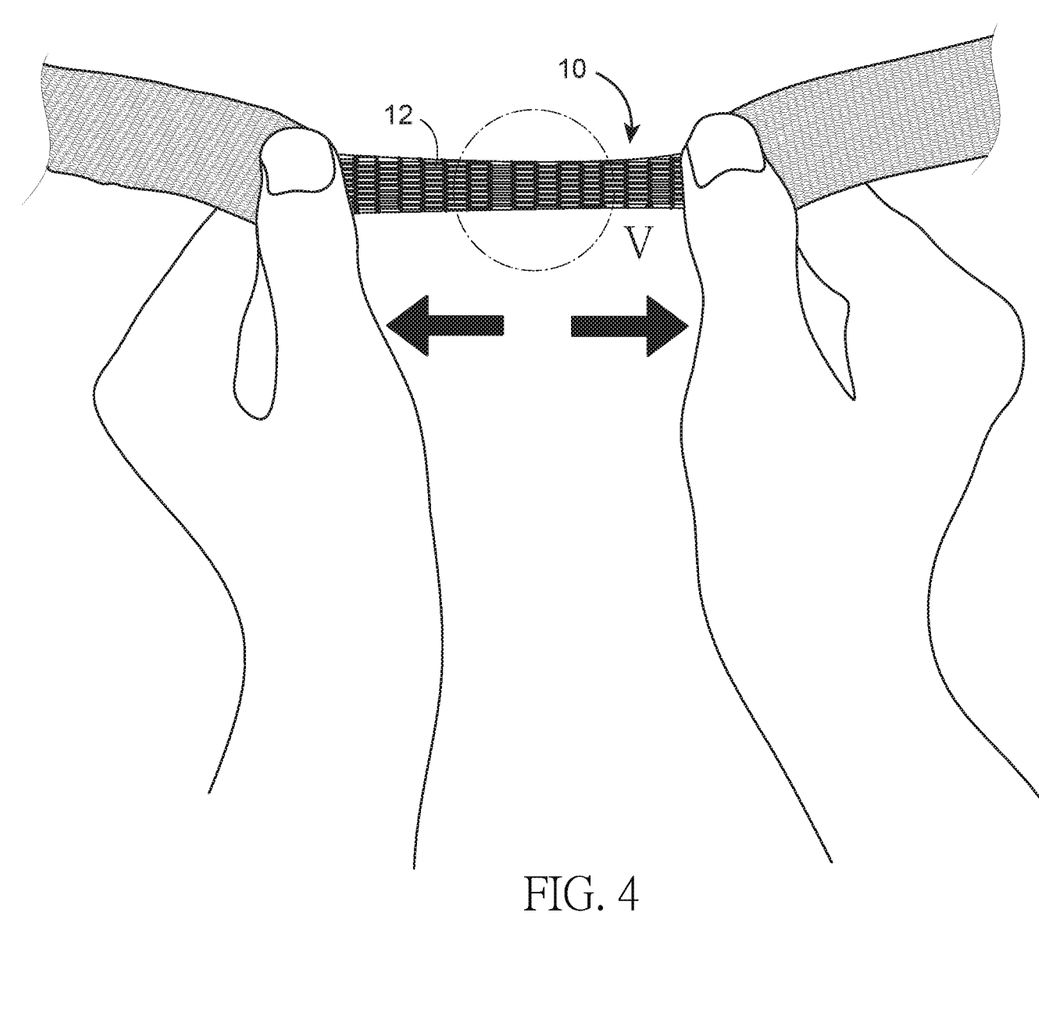
FIG. 4 is an environmental view showing the tourniquet being stretched lengthwise by two hands.
Figure 5:
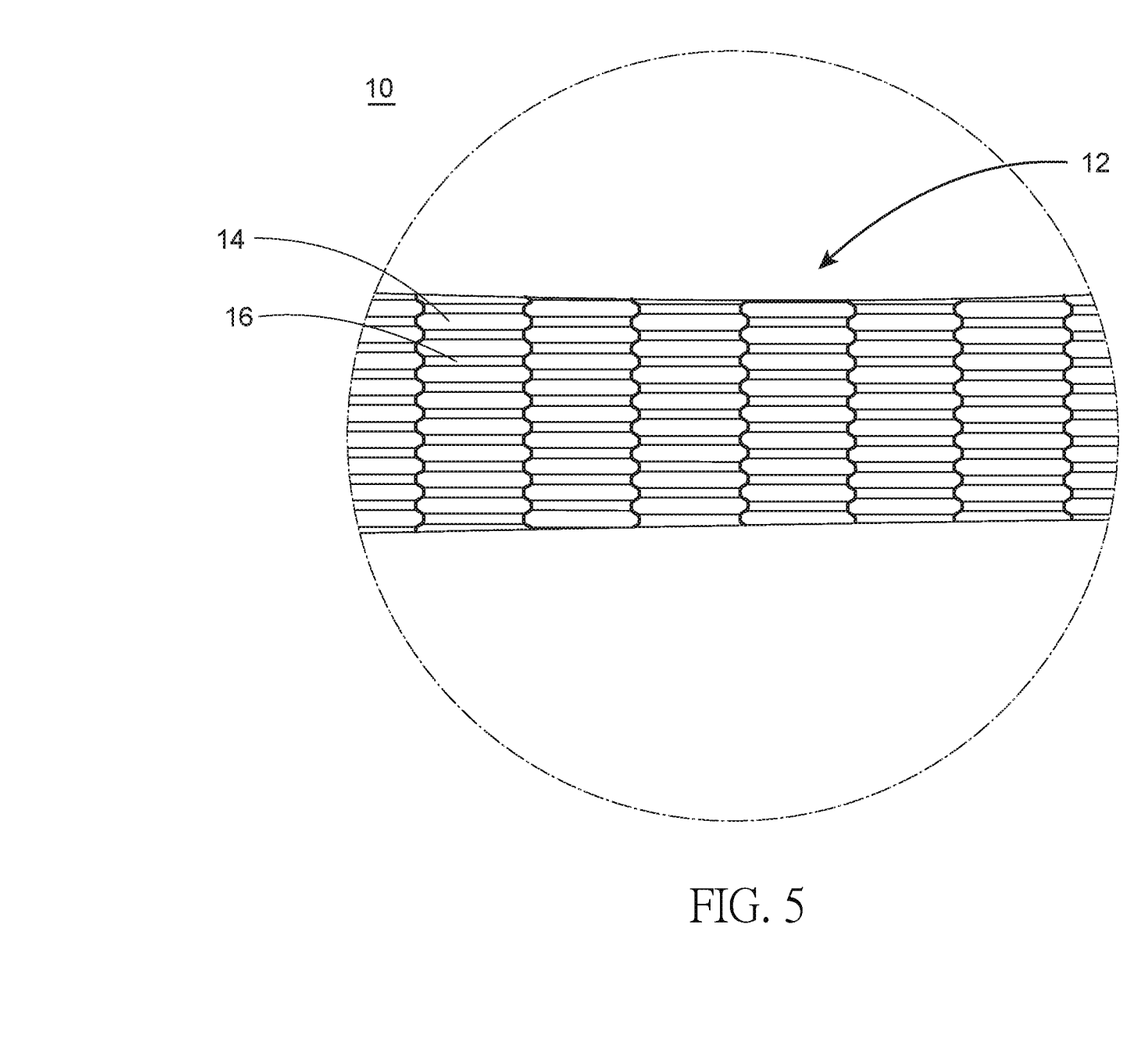
FIG. 5 is a detailed view of the area in circle V of FIG. 4.

As shown in FIGS. 3 to 5 specifically, two hands of an individual may hold two ends of the strap 10 and exert force to stretch the strap 10 lengthwise. Thus, the patterns of cavities and ridges 12 are deformed to elongate the cavities 14. And in turn, length of the first slope 141 is shortened. A plurality of ridges can be seen on the strap 10. The ridges are oriented lengthwise (i.e., the same as that of the strap 10).

Figure 6:
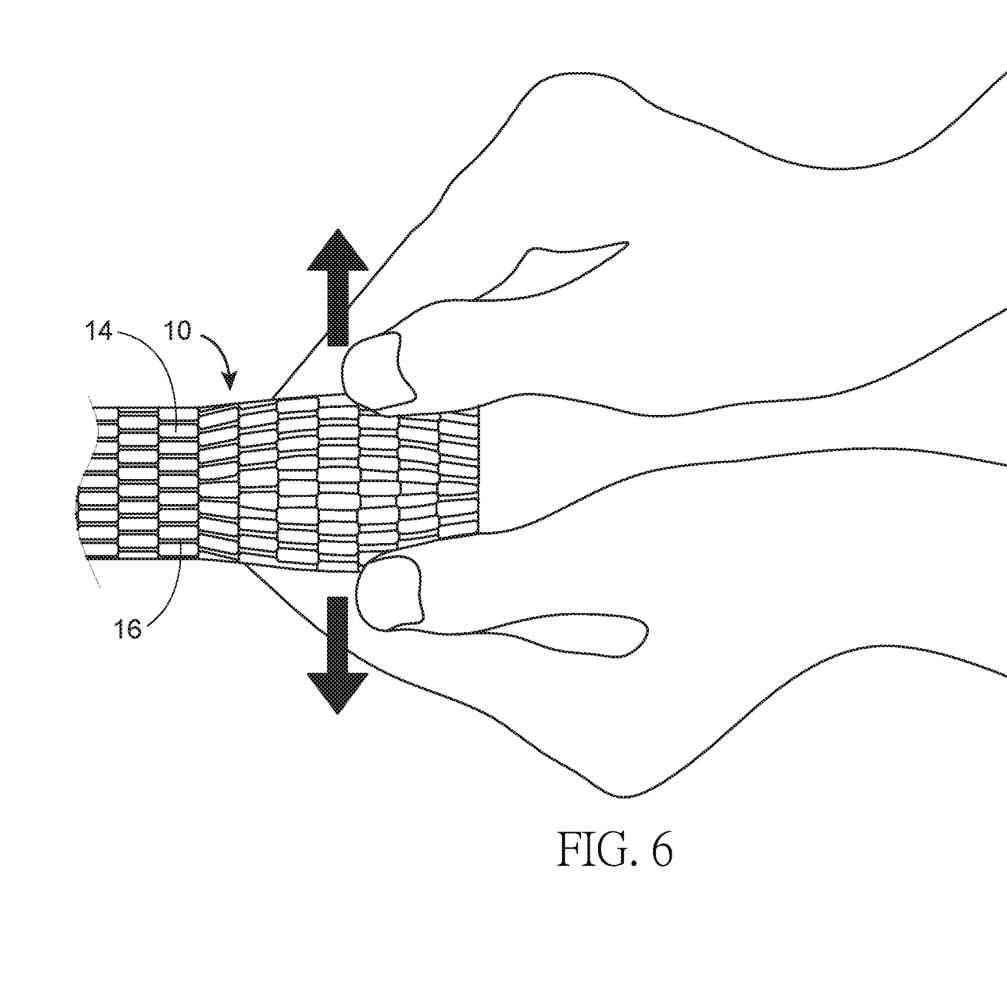
FIG. 6 is an environmental view showing the tourniquet being stretched widthwise by two hands.

As shown in FIGS. 3 and 6 specifically, two hands of the individual may hold sides of the strap 10 and exert force to stretch the strap 10 widthwise. Thus, the cavities 14 are deformed to become larger. Specifically, the first slope 141 is widened. As a result, top and bottom surfaces of the strap 10 become less uneven.

As shown in FIGS. 3 to 5 and 7 specifically, the strap 10 may be dyed for applications. For example, the strap 10 may be dyed blue for tying the arm, and the strap 10 may be dyed white for tying the leg. A medical employee can easily distinguish the desired tourniquet from many tourniquets placed together by identifying the color of the desired tourniquet. As a result, efficiency is increased greatly.

Figure 7:
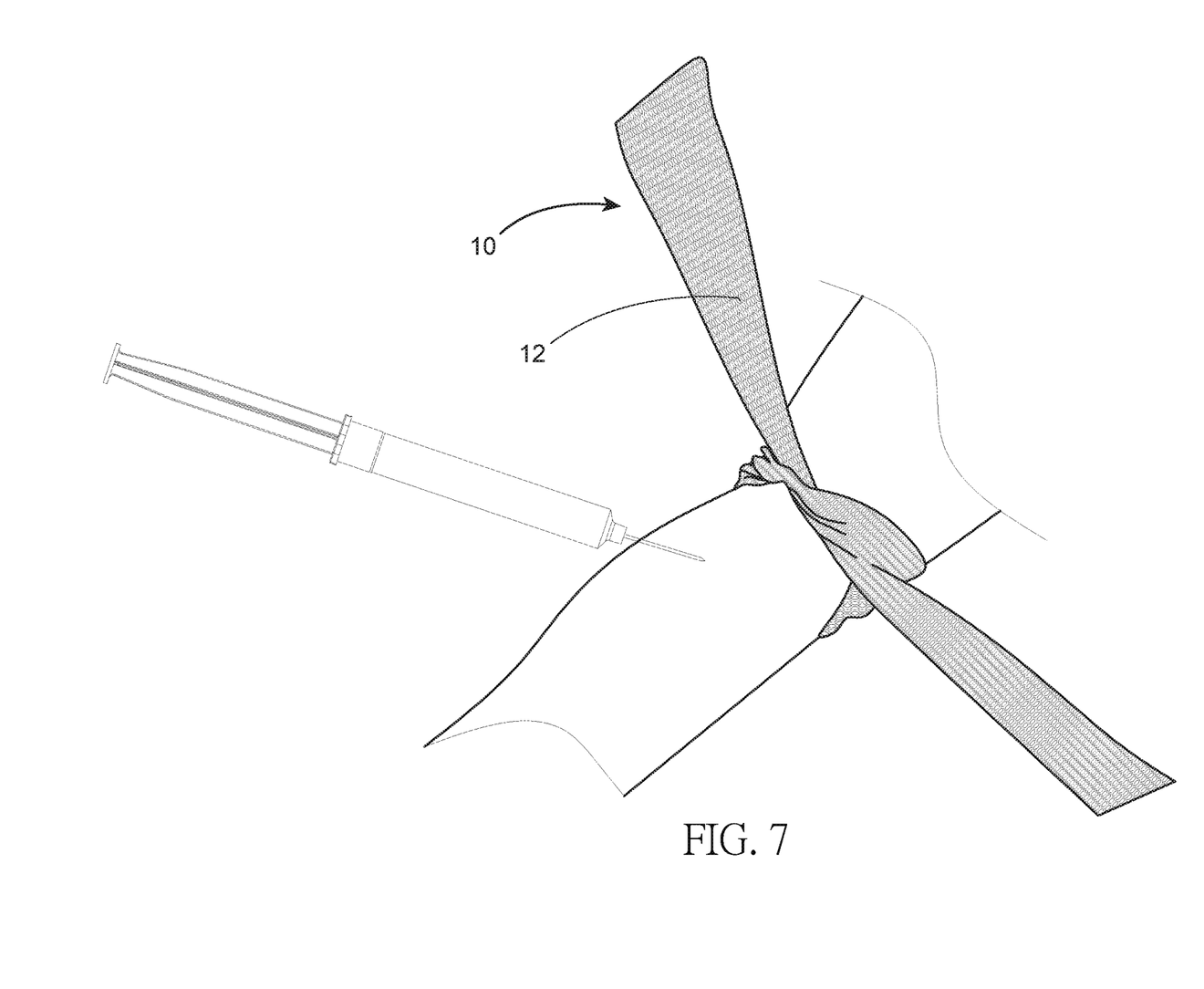
FIG. 7 is an environmental view showing a patient's limb being tied by the tourniquet before administering medical fluids by a hypodermic needle.

Before administering medical fluids by a hypodermic needle, a medical employee may tie a patient's limb with the strap 10 of the tourniquet and stretch the strap 10. Thus, the first slopes 141 become sharper. And in turn, the patterns of cavities and ridges 12 are more slip-resistant. Specifically, a medical employee may tie the limb with the strap 10 in a secure manner. Preferably, the strap 10 is made of slip-resistant material. Further, the uneven surfaces of the patterns of cavities and ridges 12 increase the effect of slip-resistant.

Preferably, width of the strap 10 is between 1 and 13 cm and thickness thereof is between 0.02 and 0.1 cm for accommodating to different body parts. For example, width of the strap 10 is about 3 cm when the tourniquet is designed to tie the wrist, and width of the strap 10 is about 10 cm when the tourniquet is designed to tie the leg. The strap 10 can be cut into pieces of desired length prior to use. The used strap 10 can be disposed for the sake of preventing it from being used again.

While the invention has been described in terms of preferred embodiments, those skilled in the art will recognize that the invention can be practiced with modifications within the spirit and scope of the appended claims.

What is claimed is:

1. A tourniquet for restricting a flow of blood in a body part, the tourniquet comprising:
    a slip-resistant, elongated strap including two patterns of cavities and ridges on top and bottom surfaces respectively, each pattern of cavities and ridges comprising:
    a plurality of spaced cavities arranged in parallel rows, each cavity being rectangular and including two first slopes on two short sides respectively and two second slopes on two elongated sides respectively, the first slopes having an elevation greater than that of the second slopes, the second slopes oriented in a direction the same as that of the strap, and the second slopes having an inclined degree greater than that of the first slopes; and
    a plurality of spaced depressions arranged in parallel rows, each depression being adjacent to one of the plurality of spaced cavities widthwise, each depression being rectangular, and each depression including two third slopes on two short sides respectively and two fourth slopes on two elongated sides respectively;
    wherein each cavity has a first depth, and each depression has a second depth less than the first depth;
    wherein the cavities and the depressions are arranged in alternating fashion;
    wherein each first slope is joined to one of the third slopes to form first ridges, and each second slope is joined to one of the fourth slopes to form second ridges, and each first ridge has an elevation greater than that of each second ridge; and
    wherein a length of each third slope is less than that of each first slope, a length of each fourth slope is less than that of each second slope, and a length of each fourth slope is greater than that of each first slope.

2. The tourniquet of claim 1, wherein corners of each cavity are arcs respectively.

3. The tourniquet of claim 1, wherein a width of the strap is between 1 and 13 cm.

4. The tourniquet of claim 1, wherein a thickness of the strap is between 0.02 and 0.1 cm.

5. The tourniquet of claim 1, wherein the strap is blue or white.

* * * * *